United States Patent [19] [11] 3,981,865
Saikawa et al. [45] Sept. 21, 1976

[54] BIS-TYPE PENICILLINS AND PROCESS FOR PRODUCING THE SAME

[75] Inventors: Isamu Saikawa; Shuntaro Takano; Okuta Takashima, all of Toyama; Kaishu Momonoi, Shinminato; Seietsu Kuroda, Toyama; Miwako Komatsu, Fuchu; Takashi Yasuda, Kosugi; Kyoko Kasuya, Takaoka; Yutaka Kodama, Toyama, all of Japan

[73] Assignee: Toyama Chemical Co., Ltd., Tokyo, Japan

[22] Filed: June 11, 1975

[21] Appl. No.: 586,015

[30] Foreign Application Priority Data
June 27, 1974  Japan................................ 49-72798
Aug. 15, 1974  Japan................................ 49-92755
Sept. 3, 1974  Japan.............................. 49-100565
May 26, 1975   Japan................................ 50-62761

[52] U.S. Cl............................... 260/239.1; 424/271
[51] Int. Cl.$^2$.............. C07D 499/66; C07D 499/68; C07D 499/70
[58] Field of Search................... 260/239.1; 424/271

[56] References Cited
UNITED STATES PATENTS
3,838,152  9/1974  Hou et al. ......................... 260/239.1

Primary Examiner—Gerald A. Schwartz
Attorney, Agent, or Firm—Oblon, Fisher, Spivak, McClelland & Maier

[57] ABSTRACT

Novel bis-type penicillins containing a (thio)acylureido group in the molecule, which are valuable antibacterial compounds for use in mammals including a human being.

This disclosure relates to such compounds and a process for the preparation thereof.

14 Claims, No Drawings

BIS-TYPE PENICILLINS AND PROCESS FOR PRODUCING THE SAME

This invention relates to novel bis-type penicillins and to a process for producing the same.

The compounds of the present invention have various characteristics including a broad antibacterial spectrum against Gram-positive and Gram-negative bacteria, and effective antibacterial activity particularly against Pseudomonas aeruginosa, Klebsiella pneumoniae and Proteus species. Furthermore, the compounds of the present invention possess high resistance to β-lactamase produced from bacteria, and show effective antibacterial activity even against clinical isolates of bacteria which are significant at present from the clinical standpoint. Accordingly, the compounds of the present invention are quite effective as therapeutic drugs for the human and animal infectious diseases caused by the above-mentioned pathogenic microorganisms.

It has heretofore been known that 6-acylamino penicillanic acids having an amino group at the α-position of the acyl group show strong antibacterial activity not only against Gram-positive bacteria but also against Gram-negative bacteria. However, there are the disadvantages that the known compounds described above have substantially ineffective antibacterial activity against not only *Pseudomonas aeruginosa*, *Klebsiella pneumoniae* and Proteus species, which have been known as causes of clinically serious infectious diseases but also resistant bacteria which are frequently isolated at present from many clinical hospitals. And they tend to be hydrolyzed with β-lactamase produced from many drug-resistant bacteria.

With an aim to obtain penicillins having no disadvantages mentioned above, the present inventors conducted extensive studies to find that novel bis-type penicillins of formula (I) which appears hereinafter, which are prepared by bonding the moiety,

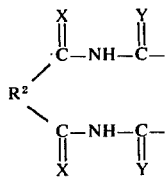

wherein $R^2$, X and Y are as mentioned hereinafter, to the amino group in the acyl group of a penicillin, can sufficiently satisfy the above-mentioned aim and have extremely valuable therapeutic effects.

It is an object of this invention to provide novel bis-type penicillins containing a (thio)acylureido group in the molecule.

It is another object of this invention to provide novel bis-type penicillins having a broad antibacterial spectrum.

It is a further object of this invention to provide novel bis-type penicillins having high resistance to β-lactamase produced from bacteria.

It is a still further object of this invention to provide novel bis-type penicillins having effective antibacterial activity against clinical isolates of bacteria.

It is a still further object of the present invention to provide a pharmaceutical composition containing a novel bis-type penicillin as active ingredient.

Other objects and advantages of this invention will become apparent from the following description.

The bis-type penicillins of the present invention are represented by the general formula (I),

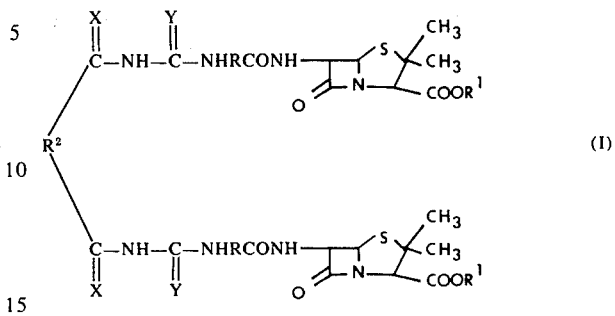

wherein R represents an amino acid residue; $R^1$ represents a hydrogen atom, a blocking group or a salt-forming cation; $R^2$ represents a substituted or unsubstituted alkylene, alkenylene, cycloalkylene, arylene, alkylenediaryl, alkylenedioxy, alkenylenedioxy, cycloalkylenedioxy, arylenedioxy or alkylenediaryldioxy group or a group represented by the formula -$R^3$-Z-$R^3$-, in which $R^3$ represents an alkylene or arylene group; Z represents an oxygen atom, a sulfur atom, a carbonyl group, or a substituted or unsubstituted arylenedioxy group; X and Y are individually an oxygen atom or a sulfur atom.

In the above-mentioned general formula (I), R represents an amino acid residue. Examples of such amino acid residue include residues of amino acids derived from various aliphatic, araliphatic, aromatic, alicyclic and heterocyclic compounds, which amino acids may have the amino group at a position such as α-, β- or γ-position to the carboxyl group. Preferable as said R is an α-amino acid residue represented by the formula

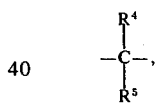

in which $R^4$ is an alkyl group such as methyl, ethyl, propyl, butyl, pentyl, hexyl, heptyl, oxtyl or the like; a cycloalkyl group such as cyclopentyl, cyclohexyl, cycloheptyl or the like; a cycloalkenyl group such as cyclopentenyl, cyclohexenyl, or the like; a cycloalkadienyl group such as cyclopentadienyl, cyclohexadienyl or the like; an aryl group such as phenyl, naphthyl or the like; an aralkyl group such as benzyl, phenethyl or the like; an aryloxy group such as phenoxy, naphthoxy or the like; an alkylthioalkyl group such as methylthiomethyl, ethylthiomethyl, methylthioethyl, ethylthioethyl or the like; or a heterocyclic group such as furyl, thienyl, oxazolyl, thiazolyl, isoxazolyl, isothiazolyl, imidazolyl, pyrazolyl, pyridyl, pyrazyl, pyrimidyl, pyridazyl, quinolyl, isoquinolyl, quinazolyl, indolyl, indazolyl, 1,3,4-oxadiazolyl, 1,2,4-oxadiazolyl, 1,3,4-thiadiazolyl, 1,2,4-thiadiazolyl or the like; each group represented by said $R^4$ may be substituted by various groups, for example, halogen, hydroxy, nitro, alkyl, alkoxy, alkylthio, acyl, alkylsulfonylamino or the like; $R^5$ represents a hydrogen atom; and $R^4$ and $R^5$ together with the common carbon atom may form a cycloalkyl ring such as cyclohexyl, cycloheptyl or the like; a cycloalkenyl ring such as cyclopentenyl, cyclohexenyl, or the like; or a cycloalkadienyl ring such as cyclopentadienyl, cyclohexadienyl, or the like.

In the general formula (I), $R^1$ is a hydrogen atom, a blocking group or a salt-forming cation. The blocking group may be any of those which have heretofore been used in the field of penicillin or cephalosporin type compounds. Concretely, the blocking group includes (1) ester-forming groups capable of being removed by catalytic reduction, chemical reduction or hydrolysis under mild conditions, e.g. arylsulfonylalkyl groups such as toluene-sulfonylethyl, etc.; substituted or unsubstituted aralkyl groups such as benzyl, 4-nitrobenzyl, diphenylmethyl, trityl, 3,5-di(tert.-butyl)4-hydroxybenzyl, etc.; substituted or unsubstituted alkyl groups such a tert.-butyl, trichloroethyl, etc.; phenacyl group; alkoxyalkyl groups such as methoxymethyl, etc.; and unsubstituted or alkyl-substituted cyclic aminoalkyl groups such as piperidinoethyl, 4-methylpiperidinoethyl, morpholinoethyl, pyrrolidinoethyl, etc.; (2) ester-forming groups capable of being easily removed owing to enzymes in a living body, e.g. acyloxyalkyl groups such as pivaloyloxymethy, etc.; phthalide group; and indanyl group; (3) organosilyl groups, organophosphoryl groups and organostannyl groups such as $(CH_3)_3Si—$,

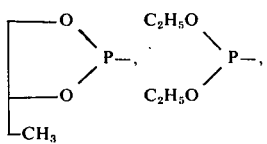

$(C_4H_9)_3Sn—$, or the like which are capable of being easily removed by treating with $H_2O$ or an alcohol. The examples of the blocking groups mentioned in above (1), (2) and (3) are merely typical, and other examples are disclosed in U.S. Pat. Nos. 3,499,909; 3,573,296 and 3,641,018 and West German Pat. Nos. 2,301,014; 2,253,287 and 2,337,105 and may be used in this invention, too. The salt-forming cation includes cations which have heretofore been known in the field of penicillin or cephalosporin type compounds, and preferable are those capable of forming non-toxic salts. The salts include alkali metal salts such as sodium salt, potassium salt, etc.; alkaline earth metal salts such as calcium salt, magnesium salt, etc.; ammonium salt; and salts with nitrogen-containing organic bases such as procaine, dibenzylamine, N-benzyl-β-phenethylamine, 1-ephenamine, N,N-dibenzylethylenediamine, etc. In addition to the above cations, there may be used cations capable of forming the salts with other nitrogen-containing organic bases, such as trimethylamine, triethylamine, tributylamine, pyridine, dimethylaniline, N-methylpyridine, N-methylmorpholine, diethylamine, dicyclohexylamine, etc.

In the general formula (I), $R^2$ is an alkylene group such as methylene, ethylene, propylene, trimethylene, tetramethylene, pentamethylene, hexamethylene, heptamethylene, octamethylene, nonamethylene, decamethylene, undecamethylene or the like; an alkenylene group such as vinylene, propenylene or the like; a cycloalkylene group such as cyclopentylene, cyclohexylene, cycloheptylene or the like; an arylene group such as (1,2-; 1,3-; 1,4-)phenylene, (1,4-; 2,6-; 2,7-; etc.-)naphthylene or the like; an alkylenediaryl group such as methylenediphenyl, ethylenediphenyl, trimethylenediphenyl, octamethylenediphenyl, methylenedinaphthyl, or the like; an alkylenedioxy group such as methylenedioxy, ethylenedioxy, trimethylenedioxy, tetramethylenedioxy, octamethylenedioxy, decamethylenedioxy or the like; an alkenylenedioxy group such as vinylenedioxy, propenylenedioxy or the like; a cycloalkylenedioxy group such as cyclopentylenedioxy, cyclohexylenedioxy, cycloheptylenedioxy or the like; an arylenedioxy group such as (1,2-; 1,3-; 1,4-)phenylenedioxy, (1,4-; 2,6-; 2,7-; etc.)naphthalenedioxy or the like; an alkylenediaryldioxy group such as methylenediphenyldioxy, ethylenediphenyldioxy, trimethylenediphenyldioxy, octamethylenediphenyldioxy, methylenedinaphthyldioxy or the like; each group represented by said $R^2$ may be substituted by various groups, for example, halogen, hydroxy, nitro, alkyl, alkoxy, alkylthio, acyl, alkylsulfonylamino or the like.

The above-mentioned compounds of the general formula (I) of the present invention have their optical isomers, and all of D-isomers, L-isomers and racemic compounds thereof are involved in the scope of the present invention.

In the present invention, preferable bis-type penicillins of the general formula (I) are as follows:

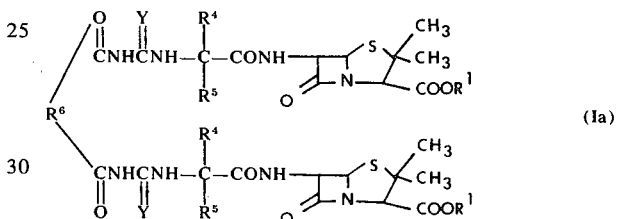

(Ia)

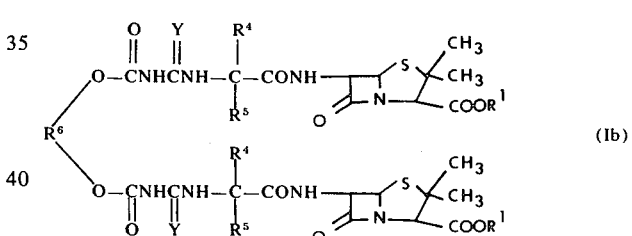

(Ib)

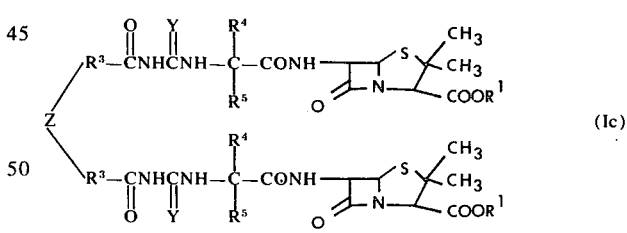

(Ic)

wherein $R^1$, $R^3$, $R^4$, $R^5$, Y and Z are as defined above, and $R^6$ represents a substituted or unsubstituted alkylene, alkenylene, cycloalkylene, arylene or alkylenediaryl group.

The compounds of formula (I) of the present invention are produced according to any of the processes (1) and (2) described below.

Process 1

A process comprising reacting a compound represented by the general formula (II),

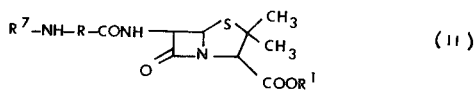

(II)

with a compound represented by the general formula (III),

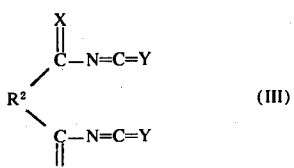

or with a reactive derivative in the

group (hereinafter referred to as "(thio)carboxyl group") of a compound represented by the general formula (IV)

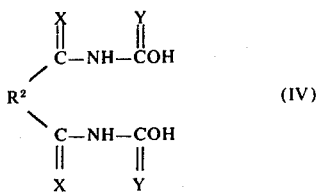

Process 2

A process comprising reacting a compound represented by the general formula (V),

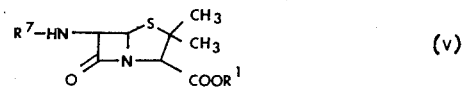

with a compound represented by the general formula (VI),

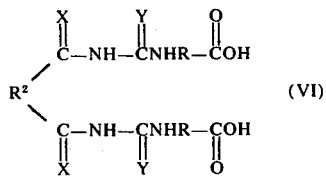

or with a reactive derivative in the

group (hereinafter referred to as "carboxyl group") of the compound of formula (VI).

In the above-mentioned formulas (II) to (VI), R, $R^1$, $R^2$, X and Y are as defined above; and $R^7$ represents a hydrogen atom or an organosilyl or organophosphoryl group having the same meaning as mentioned above for $R^1$.

As the compounds represented by the formulas (II) and (VI), there may be used any one of the D-isomer, L-isomer and racemic compound.

As the reactive derivative in the (thio)-carboxyl group of the compound of formula (IV), there is used a reactive derivative of a carboxylic acid which is ordinarily employed for the synthesis of acid amide compounds. Examples of the reactive derivative are acid halides, acid azides, acid cyanides, mixed acid anhydrides, active esters, active amides, etc. In particular, the preferred examples thereof are acid halides such as acid chlorides, acid bromides, etc., and active esters such as cyanomethyl ester, trichloromethyl ester, etc.

The compound of formula (III) and the reactive derivative in the (thio)carboxyl group of the compound of formula (IV) can be obtained by reacting, for example, the compound represented by the general formula (VII),

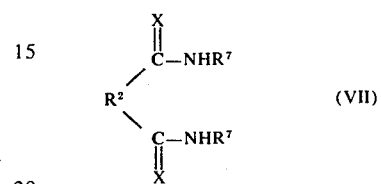

wherein $R^2$, $R^7$ and X are as defined above, with oxalylchloride, phosgene, thiophosgene, a trichloromethyl ester of chloroformic acid, an aryloxycarbonyl halide or the like.

It is possible to obtain the compound of the general formula (VI) by reacting a compound (any one of the D-isomer, L-isomer and racemic compound) represented by the general formula (VIII), $$R^7HN-R-COOR^1 \qquad (VIII)$$

wherein R, $R^1$ and $R^7$ are as defined previously, with the compound of formula (III) or the reactive derivative in the (thio)carboxyl group of a compound of formula (IV) in a solvent inert to the reaction in the presence of a base, and if necessary, hydrolyzing the resulting product. The preferred examples of the compound of formula (VI), are D-isomers, L-isomers and racemic compound of the following compounds, through it is needles to say that the examples are not limitative:

N,N'-1-methyl-1-propylmalonyl-bis[α-ureidophenylacetic acid],
N,N'-succinyl-bis[α-ureidophenylacetic acid],
N,N'-adipoyl-bis[α-ureidophenylacetic acid],
N,N'-pimeloyl-bis[α-ureidophenylacetic acid],
N,N'-sebacoyl-bis[α-ureidophenylacetic acid],
N,N'-dodecanedioyl-bis[α-ureidophenylacetic acid],
N,N'-tridecanedioyl-bis[α-ureidophenylacetic acid],
N,N'-fumaroyl-bis[α-ureidophenylacetic acid],
N,N'-1,4-cyclohexanedioyl-bis[α-ureidophenylacetic acid],
N,N'-glutaryl-bis[α-ureidophenylacetic acid],
N,N'-terephthaloyl-bis[α-ureidophenylacetic acid],
N,N'-isophthaloyl-bis[α-ureidophenylacetic acid],
N,N'-2-nitro-terephthaloyl-bis[α-ureidophenylacetic acid],
N,N'-2,5-dimethoxyterephthaloyl-bis[α-ureidophenylacetic acid],
N,N'-2,6-naphthalenedioyl-bis[α-ureidophenylacetic acid],
N,N'-1,4-phenylenedioxyacetyl-bis[α-ureidophenylacetic acid],
N,N'-4,4'-ethylenedibenzoyl-bis[α-ureidophenylacetic acid],
N,N'-4,4'-carbonyldibenzoyl-bis[α-ureidophenylacetic acid], N,N'-3,3'-thiodipropionyl-bis[α-ureidophenylacetic acid],
N,N'-sebacoyl-bis[α-ureido-p-hydroxyphenylacetic acid],
N,N'-sebacoyl-bis[1-ureidocyclohexylcarboxylic acid],
N,N'-1,4-phenylenedioxycarbonyl-bis[α-ureidophenylacetic acid],
N,N'-ethylenedioxycarbonyl-bis[α-ureidophenylacetic acid],
N,N'-cyclohexylenedioxycarbonyl-bis[α-ureidophenylacetic acid], and
N,N'-oxydiacetyl-bis[α-ureidophenylacetic acid].

As the reactive derivative in the carboxyl group of the compound represented by the general formula (VI), there is used a reactive derivative of a carboxylic acid which is ordinarily used in the synthesis of acid amides. Said reactive derivative includes, for example, acid halides, acid anhydrides, mixed acid anhydrides with organic or inorganic acids, active acid amides, acid cyanides, active esters, etc. Particularly, acid chlorides, mixed acid anhydrides or active acid amides are preferable. Examples of the mixed acid anhydrides are the mixed acid anhydrides with substituted acetic acids, alkyl carbonic acids, aryl carbonic acids and aralkyl carbonic acids; examples of the active esters are cyanomethyl esters, substituted phenyl esters, substituted benzyl esters, substituted thienyl esters, etc.; and examples of the active acid amides are N-acyl saccharins, N-acyl imidazoles, N-acyl benzoylamides, N,N'-dicyclohexyl-N-acylureas, N-acyl sulfonamides, etc.

In carrying out the present invention, the processes (1) and (2) may be carried out under substantially the same conditions. That is, the compound of formula (II) or (V) is dissolved or suspended in at least one inert solvent selected from, for example, water, acetone, tetrahydrofuran, dioxane, acetonitrile, dimethylformamide, methanol, ethanol, methoxyethanol, diethyl ether, diisopropyl ether, benzene, toluene, methylene chloride, chloroform, ethyl acetate, methyl isobutyl ketone and the like. The resulting solution or suspension is reacted with the compound of formula (III) or a reactive derivative in the (thio)carboxyl group of the compound of formula (IV), or with the compound of formula (VI) or a reactive derivative in the carboxyl group of the compound of formula (VI) in the presence or absence of a base at a temperature in the range from −60° to 80°C., preferably from −40° to 30°C. The reaction time is ordinarily 5 minutes to 5 hours. Examples of the base used in the above reaction are inorganic bases such as alkali hydroxides, alkali hydrogen-carbonates, alkali carbonates, alkali acetates, etc.; tertiary amines such as trimethylamine, triethylamine, tributylamine, pyridine, N-methylpiperidine, N-methylmorpholine, lutidine, collidine, etc.; and secondary amines such as dicyclohexylamine, diethylamine, etc. When the compound of formula (VI) is used in the form of a free acid or salt in the process (2), the reaction of the process (2) may be effected in the presence of a dehydrating condensing agent such as N,N'-dicyclohexyl carbodiimide, N-cyclohexyl-N'-morpholinoethyl carbodiimide, N,N'-diethyl carbodiimide, N,N'-carbonyl (2-methylimidazole), a trialkyl ester of phosphorous acid, ethyl ester of polyphosphoric acid, phosphorus oxychloride, phosphorus trichloride, 2-chloro-1,3,2-dioxaphospholane or oxazolyl chloride. The salt of the compound of formula (V) includes alkali metal salts, alkaline earth metal salts, ammonium salts, and salts with organic bases such as triethylamine, dicyclohexylamine and the like.

It should be understood that the reaction conditions to be employed in the processes (1) and (2) are not limited to those mentioned above, and can be properly varied depending upon the kinds of reaction reagents.

Further, the non-toxic salts of the general formula (I), in which $R^1$ is a salt-forming cation, can be easily obtained according to an ordinary procedure from compounds of the general formula (I), wherein $R^1$ is a hydrogen atom or a blocking group.

Thus, the bis-type penicillins of formula (I) can be easily obtained according to any one of the aforesaid processes (1) and (2).

The present bis-type penicillins include concretely the following compounds, though are not restricted thereto. The following penicillins can be produced by any one of the aforesaid processes (1) and (2):
N,N'-1-methyl-1-propylmalonyl-bis[6-(D(-)-α-ureidophenylacetamido) penicillanic acid],
N,N'-succinyl-bis[6-(D(-)-α-ureidophenylacetamido) penicillanic acid],
N,N'-glutaryl-bis[6-(D(-)-α-ureidophenylacetamido) penicillanic acid],
N,N'-adipoyl-bis[6-(D(-)-α-ureidophenylacetamido) penicillanic acid],
N,N'-pimeloyl-bis[6-(D(-)-α-ureidophenylacetamido) penicillanic acid],
N,N'-sebacoyl-bis[6-(D(-)-α-ureidophenylacetamido) penicillanic acid],
N,N'-dodecanedioyl-bis[6-(D(-)-α-ureidophenylacetamido) penicillanic acid],
N,N'-tridecanedioyl-bis[6-(D(-)-α-ureidophenylacetamido) penicillanic acid],
N,N'-fumaroyl-bis[6-(D(-)-α-ureidophenylacetamido) penicillanic acid],
N,N'-1,4-cyclohexanedioyl-bis[6-(D(-)-α-ureidophenylacetamido) penicillanic acid],
N,N'-sebacoyl-bis[6-(D(-)-α-ureido-p-hydroxyphenylacetamido) penicillanic acid],
N,N'-sebacoyl-bis[6-(1-ureidocyclohexylcarbonylamido) penicillanic acid],
N,N'-terephthaloyl-bis[6-(D(-)-α-ureidophenylacetamido) penicillanic acid],
N,N'-isophthaloyl-bis[6-(D(-)-α-ureidophenylacetamido) penicillanic acid],
N,N'-terephthaloyl-bis[6-(D(-)-α-thioureidophenylacetamido) penicillanic acid],
N,N'-2-nitroterephthaloyl-bis[6-(D(-)-α-ureidophenylacetamido) penicillanic acid],
N,N'-2,5-dimethoxyterephthaloyl-bis[6-(D(-)-α-ureidophenylacetamido) penicillanic acid],
N,N'-2,6-naphthalenedioyl-bis[6-(D(-)-α-ureidophenylacetamido) penicillanic acid],
N,N'-1,4-phenylenedioxyacetyl-bis[6-(D(-)-α-ureidophenylacetamido) penicillanic acid],
N,N'-4,4'-ethylenedibenzoyl-bis[6-(D(-)-α-ureidophenylacetamido) penicillanic acid],
N,N'-4,4'-carboxydibenzoyl-bis[6-(D(-)-α-ureidophenylacetamido) penicillanic acid],
N,N'-3,3'-thiodipropionyl-bis[6-(D(-)-α-ureidophenylacetamido) penicillanic acid],
N,N'-4,4'-thiodibenzoyl-bis[6-(D(-)-α-ureidophenylacetamido) penicillanic acid],
N,N'-oxydiacetyl-bis[6-(D(-)-α-ureidophenylacetamido) penicillanic acid],
N,N'-1,4-phenylenedioxycarbonyl-bis[6-(D(-)-α-ureidophenylacetamido) penicillanic acid], N,N'-ethylenedioxycarbonyl-bis[6-(D(-)-α-ureidophenylacetamido) penicillanic acid],
N,N'-cyclohexylenedioxycarbonyl-bis[6-(D(-)-α-ureidophenylacetamido) penicillanic acid],
pivaloyloxymethyl N,N'-terephthaloyl-bis[6-(D(-)-α-ureidophenylacetamido) penicillanate], and
phthalidyl N,N'-sebacoyl-bis[6-(D(-)-α-ureidophenylacetamido) penicillanate].

The susceptible test of typical compounds among the compounds of the present invention are shown below.

1. The minimum inhibitory concentrations (MIC) of the compounds against different standard strains are shown in Table 1.

The minimum inhibitory concentration (MIC) was determined by the plate method disclosed in "Chemotherapy" (Japan), Vol. 16, (1968), pages 98 – 99. The culture medium used was a Heart infusion agar (pH 7.4). The number of the cells per plate used in the inoculum was $10^4$ ($10^6$ cells/ml.).

Table 1

| Compound No. | Compound | Staphylococcus aureus 209P | Escherichia coli NIHJ | Pseudomonas aeruginosa I.F.O. | Klebsiella pneumoniae | Proteus vulgaris 3027 |
|---|---|---|---|---|---|---|
| Control | 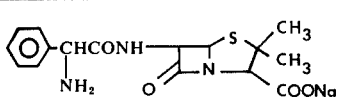 Sodium Ampicillin | <1.57 | <1.57 | >200 | 50 | >200 |
| 1 | 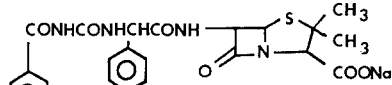 | <1.57 | 3.13 | 12.5 | 25 | 25 |
| 2 | 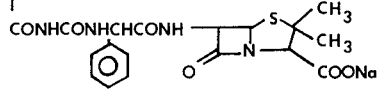 | <1.57 | <1.57 | 25 | 3.13 | 3.13 |
| 3 | 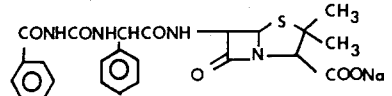 | <1.57 | 12.5 | 25 | 100 | 12.5 |
| 4 | 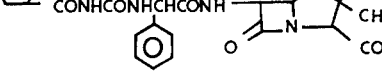 | <1.57 | 3.13 | 50 | 25 | 25 |
| 5 |  | <1.57 | 3.13 | 50 | 12.5 | 100 |

Table 1-continued

| Compound No. | Compound | Staphylococcus aureus 209P | Escherchia coli NIHJ | Pseudomonas aeruginosa I.F.O. | Klebsiella pneumoniae | Proteus vulgaris 3027 |
|---|---|---|---|---|---|---|
| 6 | 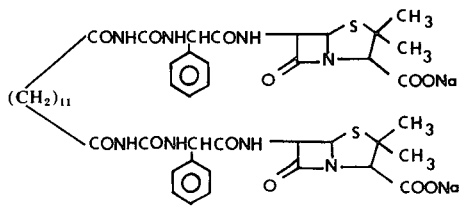 | <1.57 | 3.13 | 25 | 12.5 | 25 |
| 7 | 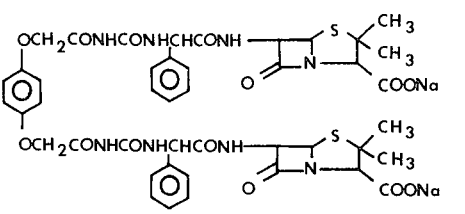 | <1.57 | 6.25 | 25 | 25 | 12.5 |
| 8 | 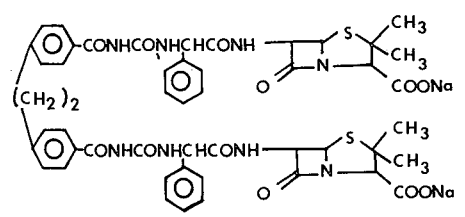 | <1.57 | <1.57 | 50 | 6.25 | 6.25 |
| 9 | 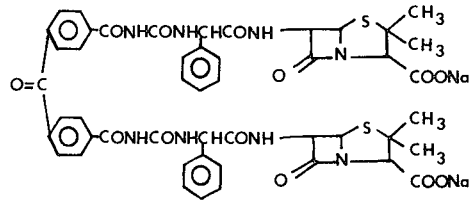 | <1.57 | 3.13 | 25 | 12.5 | 12.5 |

2. The minimum inhibitory concentrations (MIC) of the compounds against clinical isolates of bacteria are shown in Table 2.

MIC was determined in the same manner as in the preceding paragraph (1).

potassium dihydrogen phosphate, 1.2 g. of ammonium sulfate and 0.4 g. of magnesium sulfate, per liter, in a 500-ml. Erlenmeyer flask for 6 hrs. at 37°C with shaking. The resulting cells were collected by centrifugation (5,000 r.p.m. × 10 min.), washed three times with 0.1

Table 2

| Compound | GN 1035 | GN 376 | GN 82 | GN 221 | GN 1091 | Pseudomonas aeruginosa GN 2565 | GN 2987 | GN 163 | GN 264 | GN 383 | S-2 | S-3 | S-4 |
|---|---|---|---|---|---|---|---|---|---|---|---|---|---|
| Sodium Ampicillin (Control) | >200 | >200 | >200 | >200 | >200 | >200 | >200 | >200 | >200 | >200 | >200 | >200 | >200 |
| Compound No. 3 | 50 | 25 | 12.5 | 25 | 25 | 25 | 25 | 25 | 50 | 50 | 25 | 25 | 25 |

3. Resistant activity against β-lactamase, *Pseudomonas aeruginosa* GN 238 and *Escherchia coli* 33:

The resistant activity of each compound against β-lactamase was measured in the manner described below.

β-Lactamase was prepared from *Pseudomonas aeruginosa* GN 238 and *Escherchia coli* 33. This microorganism was cultured in 100 ml. of a medium containing 2 g. of yeast extract, 10 g. of polypeptone, 2 g. of glucose, 7 g. of disodium hydrogen phosphate, 2 g. of M phosphate buffer (pH 7.0). Subsequently, the cells were subjected to sonication (20 KHz, 20 min.) and then centrifuged at 15,000 r.p.m. for 60 min. By using the supernatant of enzyme fluid, the resistance of each compound against β-lactamase was determined by the iodometric assay method. The results obtained were as set forth in Table 3. Each numeral shown in Table 3 is a relative activity value calculated by assuming as 100 the activity of the control Potassium Penicillin G.

Table 3

| | Compound | Comparison of resistant activity against β-lactamase Relative activity (%) | |
|---|---|---|---|
| | | Pseudomonas aeruginosa GN238 | Escherchia coli 33 |
| Control | Potassium Penicillin G | 100 | 100 |
| | Sodium Ampicillin | 115 | 107.6 |
| | Compound No. 1 | 18 | 12 |
| | Compound No. 3 | 5 | 3 |
| | Compound No. 4 | 12 | 8 |
| | Compound No. 6 | < 1 | < 1 |

From Tables 1 and 2, it is understood that the compounds of the present invention have a broader antibacterial spectrum and more excellent antibacterial activity against not only Pseudomonas aeruginosa, Klebsiella pneumoniae, and Proteus species but also many drug-resistant bacteria than the control ampicillin. i.e. compounds having an amino group at the α-position of the acyl group. It is also understood from Table 3 that the compounds of the present invention are far higher in resistance to β-lactamase than the control drugs.

The present penicillins have generally low toxicity. For example, N,N'-succinyl-bis[6-(D(-)-α-ureidophenylacetamido) penicillanic acid] have $LD_{50}$ (i.v. in mouse having a weight of 19 ± 1 g.) greater than 3 g./kg.

The compounds of formula (I) of the present invention may be administered not only in the form of free acids but also in the form of non-toxic salts or physiologically acceptable esters. Further, the compounds which are in the form of physilogically unacceptable esters, are ordinarily put into uses after bringing them to the form of free acids or non-toxic salts by removing the ester-forming group according to a conventional procedure known in this technical field.

The compounds of the present invention can be administered to human beings and animals after formulating them into a physiological form such as tablet, capsule, syrup, injection or the like which is usually used in the case of penicillin and cephalosporin type drugs.

Procedures for producing the compounds of the present invention are shown by examples below.

EXAMPLE 1

Production of disodium salt of N,N'-sebacoyl-bis[6-(D(-)-α-ureidophenylacetamido) penicillanic acid]

In 80 ml. of methylene chloride was dissolved 5.67 g. of a triethylamine salt of D(-)-α-aminobenzyl penicillin, and into the resulting solution was dropped a solution of 1.26 g. of sebacoyl diisocyanate in 10 ml. of methylene chloride at 0°– 5°C over 10 min. Reaction was effected at room temperature for one hour, after which the solvent was removed by distillation under reduced pressure. The residue was dissolved in 100 ml. of water, and 60 ml. of ethyl acetate was added to the resulting solution, to which diluted hydrochloric acid was then added with stirring to adjust the pH of the solution to 1.5. The resulting organic layer was separated and then washed with water, after which 30 ml. of acetone was added to the washed organic layer, and the resulting solution was dried over anhydrous magnesium sulfate. A solution of 1.6 g. of sodium 2-ethylhexonate in 15 ml. of acetone was then added to the dried solution to deposit crystals. The thus deposited crystals were collected by filtration and then washed with acetone to obtain 4.7 g. (yield, 94.4 %) of a disodium salt of N,N'-sebacoyl-bis-[6-(D(-)-α-ureidophenylacetamido) penicillanic acid] having a melting point of 215°– 218°C (decomposed).

IR (KBr) $cm^{-1}$: $\nu C=O$ 1760 (β-lactam), 1700 – 1640 (—CONH—), 1600 (—COO$^-$)

NMR [$(CD_3)_2SO$ + $D_2O$, 60MC] τ values: 2.65(10H), 4.30(2H), 4.60(4H), 6.00(2H), 7.65(4H), 8.45(6H), 8.55(6H), 8.70(12H)

The above mentioned procedure was repeated, except that the sebacoyl diisocyanate was replaced by each of the compounds of formula (III) shown in Table 4, to obtain the respective objective compounds as shown in Table 4. All the objective compounds were D(-)-isomers, and the structure of each objective compound was confirmed by IR and NMR.

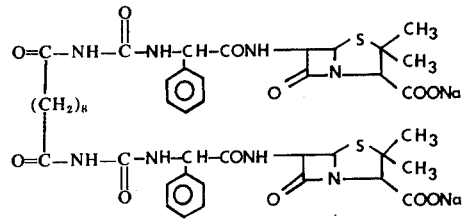

Table 4

| Compound of formula (III) | Objective compound |
|---|---|
| CONCO–(CH₂)₂–CONCO | CONHCONHCHCONH–...–COONa (CH₂)₂ CONHCONHCHCONH–...–COONa | m.p. (decomp.) 212°C, yield 74.5 %

Table 4-continued
| Compound of formula (III) | Objective compound |
|---|---|
| 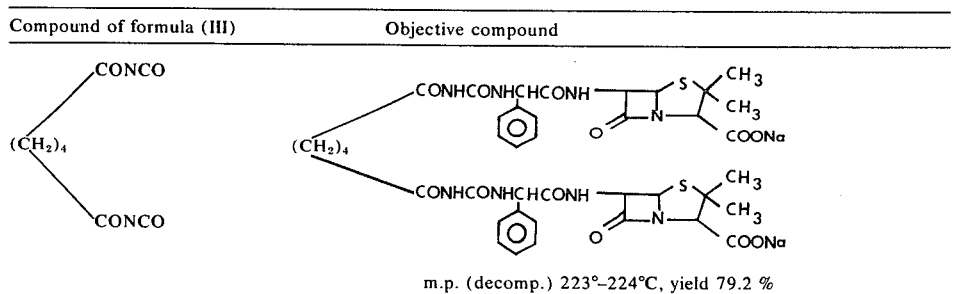 | |
m.p. (decomp.) 223°–224°C, yield 79.2 %
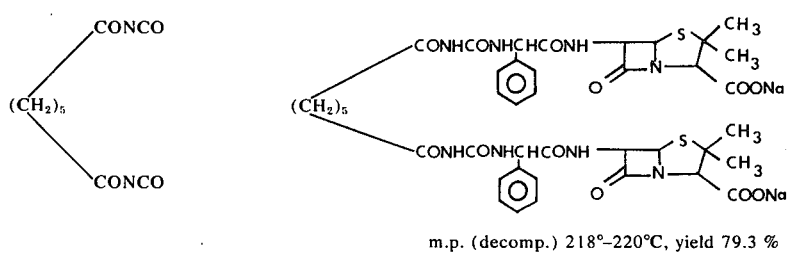
m.p. (decomp.) 218°–220°C, yield 79.3 %
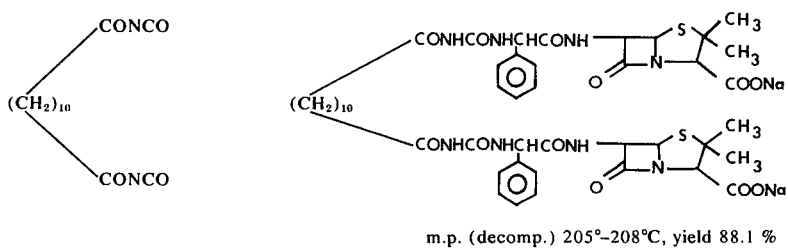
m.p. (decomp.) 205°–208°C, yield 88.1 %
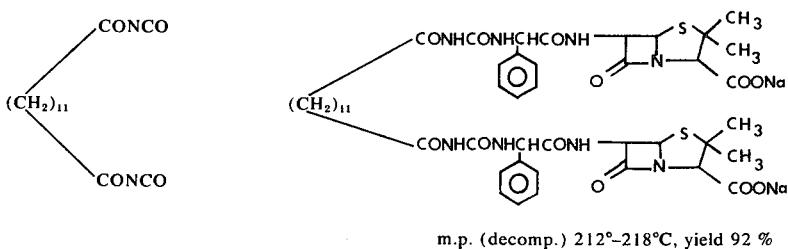
m.p. (decomp.) 212°–218°C, yield 92 %
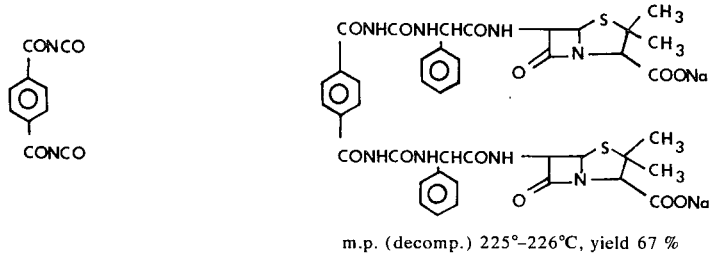
m.p. (decomp.) 225°–226°C, yield 67 %

Table 4-continued

| Compound of formula (III) | Objective compound |
|---|---|

Structure 1: CONCO / CONCO (naphthalene-like diisocyanate)
→ Bis-penicillin product with CONHCONHCHCONH linkages, COONa groups m.p. (decomp.) 219°–221°C, yield 81.6 %

Structure 2: CHCONCO / CHCONCO
→ Bis-penicillin product with CHCONHCONHCHCONH linkages, COONa groups m.p. (decomp.) 210°–214°C, yield 88.1 %

EXAMPLE 2

Production of disodium salt of N,N'-sebacoyl-bis[6-(D(-)-α-ureidophenylacetamido) penicillanic acid]

1. In 6.4 g. of hexamethyl disilazane was suspended 2 g. of D(-)-α-phenylglycine, and the resulting suspension was heated under reflux for 10 hours, after which the remaining hexamethyl disilazane was removed by distillation under reduced pressure. The thus obtained residue was dissolved in 20 ml. of dioxane, and a solution of 1.33 g. of sebacoyl diisocyanate in 5 ml. of dioxane was dropped into the resulting solution at 10° – 15°C.

Reaction was effected at room temperature for one hour, after which the solvent was removed by distillation under reduced pressure, and 40 ml. of water and 60 ml. of ethyl acetate were added to the resulting residue to form a solution. Diluted hydrochloric acid was added to the thus obtained solution with stirring to adjust the pH of the solution to 1, and the resulting organic layer was separated, washed with water and then dried over anhydrous magnesium sulfate. The solvent was removed by distillation under reduced pressure, and the resulting residue was washed with 10 ml. of diisopropyl ether to obtain 2.7 g. (yield, 92.5 %) of N,N'-sebacoyl-bis[D(-)-α-ureidophenylacetic acid] having a melting point of 201° – 204°C (decomposed).

IR (KBr) cm$^{-1}$: $\nu$NH 3280, $\nu$C=O 1710 (—COOH) $\nu$C=O 1690 – 1640 (—CONH—)

2. In 10 ml. of tetrahydrofuran was dissolved 0.5 g. of N,N'-sebacoyl-bis[D(-)-α-ureidophenylacetic acid], and 0.19 g. of N-methylmorpholine was added to the resulting solution, which was then stirred at room temperature for 10 min. A solution of 0.216 g. of ethyl chlorocarbonate in 5 ml. of tetrahydrofuran was thereafter dropped into the solution at −50° to −45°C over 5 min. Reaction was effected at 50° to −20°C for 30 min. and then at −20° to −15°C for 20 min. Thereafter, a solution of 0.86 g. of a triethylamine salt of 6-aminopenicillanic acid in 15 ml. of methylene chloride was dropped into the reaction product at 31 50° to −40°C over 10 min., after which reaction was effected at −50° to −40°C for 10 min. and then at −40° to −20°C for 20 min. The temperature of the resulting reaction solution was raised to room temperature and then subjected to distillation under reduced pressure to remove the solvent. The resulting residue was dissolved in 30 ml. of water, and to the resulting solution was added 30 ml. of ethyl acetate and then diluted hydrochloric acid was added thereto with stirring to adjust the pH to 1.5. The resulting organic layer was separated and then washed with water, after which 15 ml. of acetone was added thereto. The resulting solution was dried over anhydrous magnesium sulfate. A solution of 0.3 g. of sodium 2-ethylhexonate in 5 ml. of acetone was added to the dried solution, and the thus deposited crystals were collected by filtration and then washed with acetone to obtain 0.88 g. (yield, 97.9 %) of a disodium salt of N,N'-sebacoyl-bis[6-(D(-)-α-ureidophenylacetamido) penicillanic acid) having a melting point of 218° – 221°C (decomposed).

It was confirmed by measurement of infrared absorption spectrum that said compound was the same as that obtained in Example 1.

EXAMPLE 3

Production of disodium salt of N,N'-isophthaloyl-bis[6-(D(-)-α-ureidophenylacetamido) penicillanic acid]

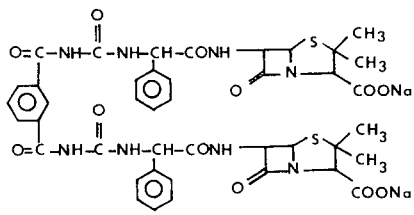

1. In 70 ml. of dioxane was suspended 8.6 g. of a hydrochloric acid salt of ethyl ester of D(-)-α-phenylglycine and 7 ml. of triethylamine was added to the resulting suspension, which was then stirred for 30 min. To the suspension was added 3.9 g. of isophthaloyl isocyanate with water-cooling over 5 min. and the suspension was subjected to reaction at room temperature for one hour. The resulting insolubles were filtered off and the filtrate was concentrated under reduced pressure to dryness. To the residue was added 50 ml. of water to form a solution and then diluted hydrochloric acid was added to the resulting solution with stirring to adjust the pH thereof to 1. The thus deposited crystals were collected by filtration and then recrystallized from 40 ml. of methyl Cellosolve to obtain 8.5 g. (yield, 81 %) of ethyl N,N'-isophthaloyl-bis[D(-)-α-ureidophenylacetate] having a melting point of 180° – 182°C.

IR (KBr) cm$^{-1}$: $\nu$C=O 1730 (—COOC$_2$H$_5$), 1690 – 1650 (—CONH—)

Elementary analysis (C$_{30}$H$_{30}$O$_8$N$_4$): Found: C, 62.61 %; H, 5.26 %; N, 9.66 %; Calcd.: C, 62.71 %; H, 5.26 %; N, 9.75 %

In a mixture of 15 ml. of acetic acid and 3 ml. of conc. hydrochloric acid was suspended 1.5 g. of ethyl N,N'-isophthaloyl-bis[D(-)-α-ureidophenylacetate] and the resulting suspension was heated, upon which suspension was converted into a solution, and then white crystals were deposited in the solution. The solution was subjected to reaction under reflux for 30 min., and then cooled. The thus deposited crystals were collected by filtration and then washed with acetic acid to obtain 600 mg. (yield, 44.4 %) of N,N'-isophthaloyl-bis[D(-)-α-ureidophenylacetic acid] having a melting point of 223° – 238°C (decomposed).

IR (KBr) cm$^{-1}$: $\nu$NH 3250 $\nu$C=O 1730 – 1650 (—COOH, —CONH—)

2. In 10 ml. of ethanol was suspended 520 mg. of N,N'isophthaloyl-bis[D(-)-α-ureidophenylacetic acid] and 0.36 ml. of triethylamine was added to the suspension to form a solution. The ethanol was removed by distillation under reduced pressure and the residue was dried over phosphorus penoxide to obtain a ditriethylamine salt of N,N'-isophthaloyl-bis[D(-)-α-ureidophenylacetic acid]. This salt was suspended in 20 ml. of tetrahydrofuran, and 240 mg. of ethyl chlorocarbonate was dropped into the suspension at −30°C. The reaction was effected at −30° to −15°C for 1 hour and then at −15°C for one hour, after which a solution of 950 mg. of a triethylamine salt of 6-aminopenicillanic acid in 15 ml. of methylene chloride was dropped thereinto over 5 min. at −50°C to −30°C. The reaction was effected at said temperature for 30 min. and then at −30° to −10°C for 1 hour, after which the temperature of the reaction solution was raised to room temperature and then subjected to distillation under reduced pressure to remove the solvent. The residue was dissolved in 30 ml. of water and 30 ml. of ethyl acetate was then added to the solution, after which diluted hydrochloric acid was added thereto to adjust the pH thereof to 1.5. The resulting organic layer was separated, washed with water, dried over anhydrous magnesium sulfate, and thereafter subjected to distillation under reduced pressure to remove the solvent. The residue was dissolved in a mixed solution of 25 ml. of methylene chloride and 0.28 ml. of triethylamine, to which a solution of 300 mg. of sodium 2-ethylhexonate in 5 ml. of butanol was added. The thus deposited crystals were collected by filtration and then washed with methylene chloride to obtain 770 mg. (yield, 80.2 %) of a disodium salt of N,N'-isophthaloyl-bis[6-(D(-)-α-ureidophenylacetamido) penicillanic acid] having a melting point of 218°C (decomposed).

IR (KBr) cm$^{-1}$: $\nu$C=O 1760 ($\beta$-lactam), 1670 – 1600 (—COO , —CONH—).

EXAMPLE 4

Production of N,N'-4,4'-phenylenedioxyacetyl-bis[6(D(-)-α-ureidophenylacetamido) penicillanic acid]

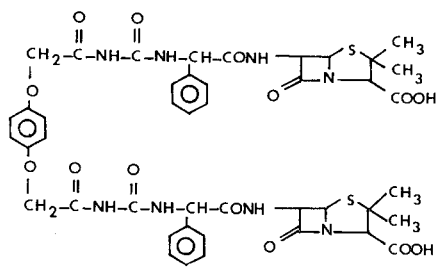

1. In 40 ml. of methylene chloride was dissolved 3.1 g. of a triethylamine salt of D(-)-α-aminobenzyl penicillin, and 0.6 g. of p-phenylenedioxydiacetyl isocyanate was dropped into the solution at 0° – 5°C. The solution was subjected to reaction with cooling with ice for 30 min. and then at room temperature for 1 hour, after which the solvent was removed by distillation under reduced pressure. The residue was dissolved in 40 ml. of water to form a solution, and 40 ml. of ethyl acetate was added to the resulting solution. Diluted hydrochloric acid was added to the solution with stirring to adjust the pH thereof to 1.5. The resulting organic layer was separated, washed with 10 ml. of acetone and then dried over anhydrous magnesium sulfate, after which the solvent was removed by distillation under reduced pressure to obtain 1.6 g. (yield, 75.5 %) each objective compound was confirmed by IR and NMR.

Table 5

| Compound of formula (III) | Objective compound |
|---|---|
| 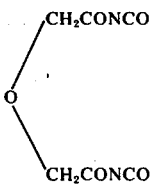 | 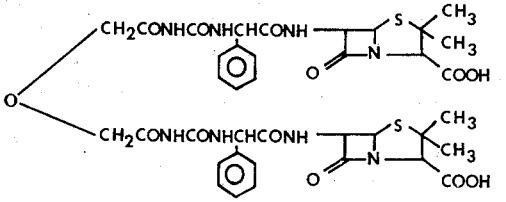<br>m.p. (decomp.) 184°–190°C, yield 89.6 % |
| 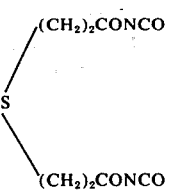 | 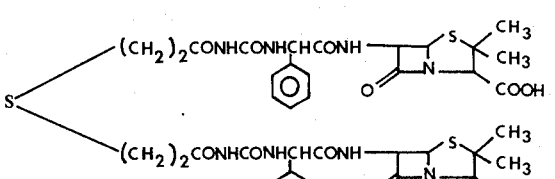<br>m.p. (decomp.) 178°–180°C, yield 71.4 % |
| 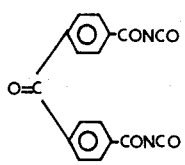 | 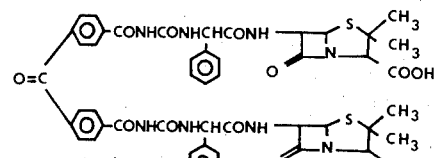<br>m.p. (decomp.) 208°C, yield 78.4 % | of N,N'-4,4'-phenylenedioxyacetyl-bis[6(D(-)-α-ureidophenylacetamido) penicillanic acid] having a melting point of 155° – 158°C (decomposed).

IR (KBr) cm⁻¹: νC=O 1780 (β-lactam), 1720 (—COOH), 1710 – 1650 (—CONH—).

NMR [(CD₃)₂CO + D₂O, 60MC] τ values: 2.62(10H), 3.03(4H), 4.22 – 4.61(6H), 5.32(4H), 5.70(2H), 8.49(6H), 8.56(6H).

2. In 40 ml. of acetone was dissolved 1.6 g. of N,N'-4,4'-phenylenedioxyacetyl-bis[6(D(-)-α-ureidophenylacetamido) penicillanic acid] and a solution of 0.61 g. of sodium 2-ethylhexonate in 10 ml. of acetone was added to the solution. The resulting crystals were collected by filtration and then washed with acetone to obtain 1.6 g. (yield, 95.8 %) of a disodium salt of N,N'-4,4'-phenylenedioxyacetyl-bis[6-(D(-)-α-ureidophenylacetamido) penicillanic acid] having a melting point of 212° – 214°C (decomposed).

IR (KBr) cm⁻¹: νC=O 1760 (β-lactam), 1710 – 1660 (—CONH—), 1600 (—COO⁻)

The above-mentioned procedure (1) was repeated, except that the p-phenylenedioxydiacetyl isocyanate was replaced by each of the compounds of formula (III) shown in Table 5, to obtain the respective objective compounds as shown in Table 5. All the objective compounds were D(-) isomers, and the structure of

EXAMPLE 5

Production of disodium salt of N,N'-4,4'-phenylenedioxyacetyl-bis[6-(D(-)-α-ureidophenylacetamido) penicillanic acid]

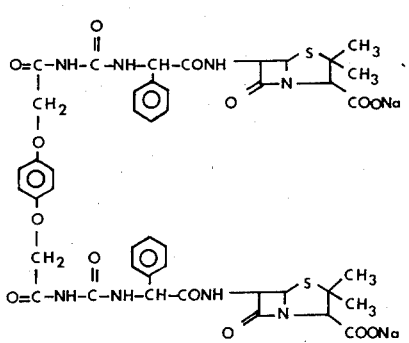

1. In 6.4 g. of hexamethyl disilazane was suspended 2 g. of D(-)-α-phenylglycine, and the resulting solution was subjected to reaction under reflux for 10 hours. The remaining hexamethyl disilazane was removed by distillation under reduced pressure, and the residue was dissolved in 20 ml. of dioxane. To the resulting solution was added 1.35 g. of p-phenylenedioxydiacetyl isocyanate at 10° – 15°C. Reaction was effected at room temperature for 1 hour, after which the reaction solution was concentrated under reduced pressure to a half volume and then poured into 70 ml. of water. Diluted hydrochloric acid was added thereto with stirring to adjust the pH thereof to 1 to deposit crystals, and the thus deposited crystals were collected by filtration, washed with water and then dried to obtain 2.8 g.(yield, 98.9 %) of N,N'-4,4'-phenylenedioxyacetyl-bis[D(-)-α-ureidophenylacetic acid] a melting point of 227.5° – 228.5°C (decomposed).

IR (KBr) cm⁻¹: $\nu$NH 3300 $\nu$C=O 1720 (—COOH), 1700 – 1650 (—CONH—).

2. In 10 ml. of tetrahydrofuran was suspended 0.5 g. of N,N'-4,4'-phenylenedioxyacetyl-bis[D(-)-α-ureidophenylacetic acid], and thereto was added 0.183 g. of N-methylmorpholine. The resulting solution was stirred at room temperature for 1 hour, and thereinto was dropped a solution of 0.206 g. of ethyl chlorocarbonate in 5 ml. of tetrahydrofuran at −50° to −45°C over 5 min. Reaction was effected at −50° to −20°C for 30 min. and then at −20° to −15°C for 20 min., after which a solution of 0.83 g. of a triethylamine salt of 6-aminopenicillanic acid in 15 ml. of methylene chloride was dropped thereinto at −50° to −40°C over 10 min. Reaction was effected at −50° to −40°C for 10 min. and then at −40° to −20°C for 20 min., after which the temperature of the reaction solution was raised to room temperature and then subjected to distillation under reduced pressure to remove the solvent. The residue was dissolved in 30 ml. of water and 30 ml. of ethyl acetate was added thereto with stirring to the resulting solution, to which diluted hydrochloric acid was then added to adjust the pH thereof to 1.5. The resulting organic layer was separated, and thereafter washed with water. To the thus washed organic layer was added 10 ml. of acetone, and the solution as dried over anhydrous magnesium sulfate. A solution of 0.29 g. of sodium 2-ethylhexonate in 5 ml. of acetone was thereafter added to the thus dried solution, and the thus deposited crystals were collected by filtration and then washed with acetone to obtain 0.75 g. (yield, 85.2 %) of a disodium salt of N,N'-4,4'-phenylenedioxyacetyl-bis[6-(D(-)-α-ureidophenylacetamido) penicillanic acid] having a melting point of 211° – 214°C.

The above compound had the same infrared absorption spectrum as that of the penicillin compound obtained in Example 4.

EXAMPLE 6

Production of disodium salt of N,N'-1,4-phenylenedioxycarbonyl-bis[6-(D(-)-α-ureidophenylacetamido) penicillanic acid]

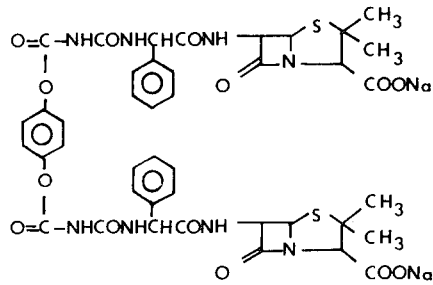

In 30 ml. of methylene chloride was dissolved 1.7 g. of a triethylamine salt of D(-)-α-aminobenzylpenicillin, and into the resulting solution was dropped a solution of 0.28 g. of 1,4-phenylenedioxycarbonyl isocyanate in 2 ml. of dioxane at 0° – 5°C over 3 min. Reaction was effected at room temperature for 1 hour, after which the solvent was removed by distillation under reduced pressure, and the residue was dissolved in 30 ml. of water. To the resulting solution was added 30 ml. of ethyl acetate, and then diluted hydrochloric acid was added thereto with stirring while cooling with ice to adjust the pH of the solution to 1.5. The resulting organic layer was separated, and washed with water, after which 10 ml. of acetone was added thereto, and the resulting solution was dried over anhydrous magnesium sulfate. A solution of 0.38 g. of sodium 2-ethylhexonate in 10 ml. of acetone was added to the dried solution and the deposited crystals were collected by filtration and then washed with acetone to obtain 1.0 g. (yield, 89.3 %) of a disodium salt of N,N'-1,4-diphenylenedioxycarbonyl-bis[6-(D(-)-α-ureidophenylacetamido) penicillanic acid] having a melting point of 208° – 212°C (decomposed).

IR (KBr) cm⁻¹: $\nu$C=O 1760 (β-lactam), 1690 – 1650 (—CONH—), 1600 (—COO⁻).

NMR [(CD₃)₂SO + D₂O, 60MC] τ values: 2.68(10H), 3.15(4H), 4.20 – 4.70(6H), 6.00(2H), 8.48(6H), 8.60(6H).

EXAMPLE 7

Production of N,N'-ethylenedioxycarbonyl-bis[6-(D(-)-α-ureidophenylacetamido) penicillanic acid]

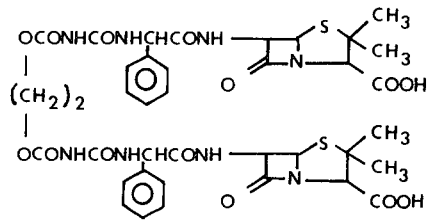

In 70 ml. of anhydrous methylene chloride was dissolved 6.73 g. of a triethylamine salt of D(-)-α-aminobenzylpenicillin, and into the resulting solution was dropped a solution of 1.24 g. of ethylenedioxycarbonyl isocyanate in 7 ml. of anhydrous methylene chloride over 5 min. while cooling the solution with ice. Reaction was effected at room temperature for one hour, after which the solvent was removed by distillation under reduced pressure. The residue was dissolved in 50 ml. of water and then washed with ethyl acetate. To the aqueous layer was again added 50 ml. of ethyl acetate, and diluted hydrochloric acid was then added thereto with stirring while cooling it with ice to adjust the pH of solution to 1.5. The resulting organic layer was separated, and washed with water, and then dried over anhydrous magnesium sulfate. The solvent was removed by distillation under reduced pressure, and ether was added to the residue to obtain crystals. The resulting crystals were collected by filtration to obtain 4.4 g. (yield, 81.5 %) of N,N'-ethylenedioxycarbonyl-bis[6(D(-)-α-ureidophenylacetamido) penicillanic acid] having a melting point of 165° – 170°C (decomposed).
- IR (KBr) cm$^{-1}$: $\nu$C=O 1775 ($\beta$-lactam), 1730 – 1655 (—COOH, —CONH—)
- NMR [(CD$_3$)$_2$SO, 60MC] $\tau$ values: −0.27(2H), 0.68(2H), 1.26(2H), 2.60(10H), 4.02 – 4.62(6H), 5.64(4H), 5.76(2H), 8.42(6H), 8.57(6H).

EXAMPLE 8

In the same manner as in Example 7, 2.06 g. of N,N′-ethylenedioxycarbonyl-bis[6-(D(-)-α-ureidophenylacetamido) penicillanic acid] was obtained from 1.0 g. of N,N′-ethylenedioxycarbonyl-bis[D(-)-α-ureidophenylacetic acid] and 1.02 g. of a triethylamine salt of 6-aminopenicillanic acid (yield, 72.5 %).

The IR spectrum of this compound was identical with that of the compound obtained in Example 7.

EXAMPLE 9

Production of N,N′-1,4-phenylenedicarbonyl-bis[6(D(-)-α-thioureidophenylacetamido) penicillanic acid]

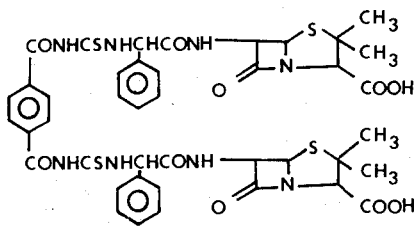

In 50 ml. of anhydrous methylene chloride was dissolved 1.13 g. of a triethylamine salt of D(-)-α-aminobenzylpenicillin, annd into the resulting solution was dropped a solution of 0.88 g. of 1,4-phenylenedicarbonyl isothiocyanate in 3 ml. of benzene over 5 min. while cooling it with ice. After reaction was effected at room temperature for 1 hour, the solvent was removed by distillation under reduced pressure, and the residue was dissolved in 50 ml. of water and then washed with ethyl acetate, after which 50 ml. of ethyl acetate was again added to the solution. Diluted hydrochloric acid was thereafter added to the solution with stirring to adjust the pH thereof to 1.5. The resulting organic layer was separated, washed with water and then dried over anhydrous magnesium sulfate. The solvent was removed by distillation under reduced pressure, and diisopropyl ether was added to the residue. The resulting crystals were collected by filtration to obtain 0.61 g. (yield, 64.5 %) of N,N′-1,4-phenylenedicarbonyl-bis[6-(D(-)-α-thioureidophenylacetamido) penicillanic acid] having a melting point of 200° – 210°C (decomposed).

- IR (KBr) cm$^{-1}$: $\nu$C=O 1775 ($\beta$-lactam), 1730 – 1640 (—COOH, —CONH—),
- NMR [(CD$_3$)$_2$SO, 60MC] $\tau$ values: -1.83(2H), 0.53(2H), 0.92(2H), 1.98(4H), 2.63(10H), 4.08(2H), 4.04 – 4.54(4H), 5.78(2H), 8.45(6H), 8.57(6H)

The above-mentioned procedure was repeated, except that the 1,4-phenylenedicarbonyl isothiocyanate was replaced by each of the compounds of formula (III) shown in Table 6, to obtain the respective objective compounds as shown in Table 6. All the objective compounds were D(-)-isomers, and the structure of each objective compound was confirmed by IR and NMR.

Table 6

| Compound of formula (III) | Objective compound |
| --- | --- |

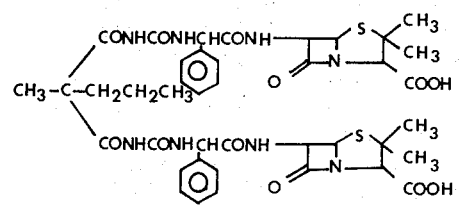

m.p. (decomp.) 176°–179°C, yield 79.1 %

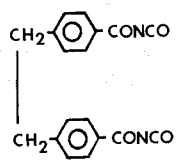 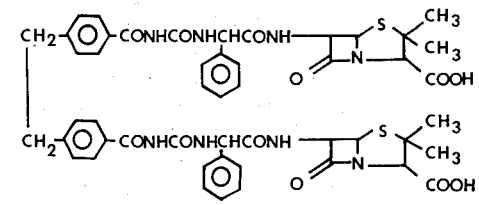

m.p. (decomp.) 167°C, yield 78.3 %

Table 6-continued

| Compound of formula (III) | Objective compound |
|---|---|
| | m.p. (decomp.) 198°–200°C, yield 85.2 % |

EXAMPLE 10

Production of dipotassium salt of N,N'-sebacoyl-bis[6-(D(-)-α-ureido-p-hydroxyphenylacetamido) penicillanic acid]

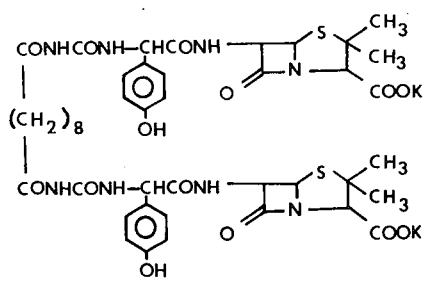

In 50 ml. of acetonitrile was dissolved 1.78 g. of a triethylamine salt of D(-)-α-amino-p-hydroxybenzylpenicillin, and to the resulting solution was added dropwise a solution of 0.40 g. of sebacoyl diisocyanate in 3 ml. of methylene chloride at −2° to 0°C over 5 min. Reaction was effected for one hour while cooling the solution with ice, after which the solvent was removed by distillation under reduced pressure, and the residue was dissolved in 20 ml. of water. To the solution was added 30 ml. of ethyl acetate. Diluted hydrochloric acid was added to the solution with stirring while cooling it with ice to adjust the pH thereof to 2.0, and the resulting organic layer was separated, washed with water and then dried over anhydrous magnesium sulfate. The solvent was removed by distillation under reduced pressure, and 30 ml. of acetone was added to the residue to dissolve the latter in the former, after which 0.41 g. of potassium 2-ethylhexonate in 2 ml. of acetone was added to the solution. The thus deposited crystals were collected by filtration, and washed with acetone to obtain 1.1 g. (yield, 65.5 %) of a dipotassium salt of N,N'-sebacoylbis [6-(D(-)-α-ureido-p-hydroxyphenylacetamido) penicillanic acid] having a melting point of 203° – 206°C (decomposed).

IR (KBr) cm$^{-1}$: $\nu$C=O 1760 ($\beta$-lactam), 1700 – 1650 (—CONH—), 1600 (—COO$^{\ominus}$)

EXAMPLE 11

Production of N,N'-sebacoyl-bis[6-(1-ureidocyclohexylcarbonylamido) penicillanic acid]

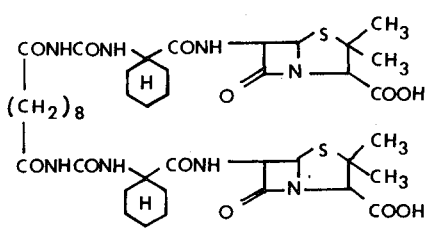

In 30 ml. of methylene chloride was dissolved 2.66 g. of a triethylamine salt of 1-aminocyclohexylpenicillin, and into the solution was dropped at −3° to 2°C a solution of 0.63 g. of sebacoyl diisocyanate in 3 ml. of methylene chloride over 5 min. Reaction was effected for one hour while cooling the solution with ice, after which the solvent was removed by distillation under reduced pressure. The residue was dissolved in 30 ml. of water to form a solution, and 50 ml. of ethyl acetate was added to the solution. Diluted hydrochloric acid was added thereto with stirring to adjust the pH thereof to 1.5. The resulting organic layer was separated, washed with water and then dried over anhydrous magnesium sulfate. The solvent was removed by distillation under reduced pressure, 30 ml. of ether was added to the residue, and the resulting crystals were collected by filtration to obtain 1.75 g. (yield, 75.9 %) of N,N'-sebacoyl-bis[6-(1-ureidocyclohexylcarbonylamido) penicillanic acid] having a melting point of 140° – 145°C (decomposed).

IR (KBr) cm$^{-1}$: $\nu$C=O 1770 ($\beta$-lactam), 1730 – 1630 (—COOH, —CONH—)

EXAMPLE 12

Production of dipivaloyloxymethyl N,N'-terephthaloyl-bis[6-(D(-)-α-ureidophenylacetamido) penicillanate]

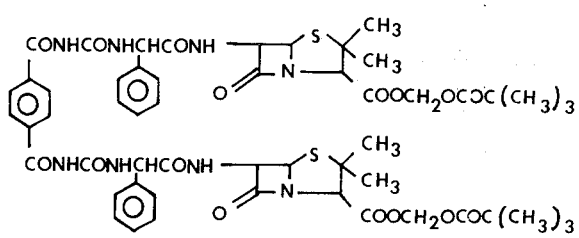

In 100 ml. of anhydrous methylene chloride was dissolved 5.0 g. of a pivaloyloxymethyl D(-)-α-aminophenylacetamido penicillanate hydrochloride, and to the solution was added 1.0 g. of triethylamine while cooling the solution with ice, after which the solution was stirred for 15 min. at the same temperature. A solution of 0.76 g. of terephthaloyl diisocyanate in 12 ml. of anhydrous benzene was dropped thereinto over 10 min. while cooling it with ice, and at the same temperature, reaction was effected for 1 hour. The temperature of the reaction solution was then gradually elevated to room temperature, and the solvent was removed by distillation under reduced pressure. To the residue was added 50 ml. of ethyl acetate to dissolve the former in the latter, and 50 ml. of water was then added to the solution, after which 2N hydrochloric acid was added thereto to adjust the pH of the solution to 1.5. The resulting organic layer was separated, washed with water, and then dried over anhydrous magnesium sulfate. The solvent was removed by distillation under reduced pressure and ether was added to the residue. The thus deposited crystals were collected by filtration and then dried to obtain 3.80 g. (yield, 90.3 %) of a dipivaloyloxymethyl N,N'-terephthaloyl-bis[6-(D(-)-α-ureidophenylacetamido) penicillanate] having a melting point of 170° – 175°C (decomposed).

IR (KBr) cm$^{-1}$: $\nu$C=O 1780 – 1730 ($\beta$-lactam, ester), 1710 – 1630 (—CONH—)

In the same manner as above, 2.7 g. of a diphthalidyl N,N'-sebacoyl-bis[6-(D(-)-α-ureidophenylacetamido) penicillanate] was obtained from 3.11 g. of a phthalidyl D(-)-α-aminophenylacetamido penicillanate hydrochloride and 0.63 g. of sebacoyl diisocyanate (yield, 88.8 %), m.p. 145° – 150°C (decomposed).

IR (KBr) cm$^{-1}$: $\nu$C=O 1790 – 1760 ($\beta$-lactam, lactone) 1710 – 1640 (ester, —CONH—)

EXAMPLE 13

Production of
N,N'-1,4-cyclohexylenedioxycarbonyl-bis[6-D(-)-α-ureidophenylacetamidopenicillanic acid]

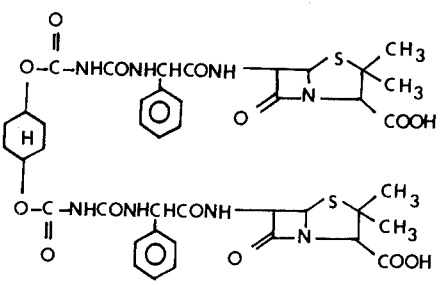

In the same manner as in Example 7, N,N-1,4-cyclohexylenedioxycarbonyl-bis[6-D(-)-α-ureidophenylacetamidopenicillanic acid] was obtained by reacting a triethylamine salt of D(-)-α-aminobenzylpenicillin with cyclohexylenedioxycarbonylisocyanate. (yield, 76 %) m.p. 137° – 143°C IR (KBr) cm$^{-1}$: $\nu$C=O 1780 ($\beta$-lactam) 1730 – 1660 (—COOH, —CONH—)

What is claimed is:

1. A compound represented by the general formula (I),

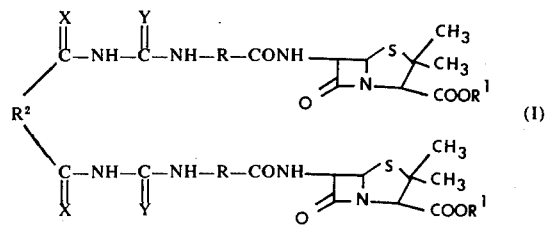

wherein R is the radical derived from a conventional penicillin acylamido group represented by the formula

in which $R^4$ represents a substituted or unsubstituted alkyl, cycloalkyl, cycloalkenyl, cycloalkadienyl, aryl, aralkyl, aryloxy, alkylthioalkyl, or a heterocyclic group; and $R^5$ represents a hydrogen atom; $R^4$ and $R^5$ together with the common carbon atom may form a cycloalkyl, cycloalkenyl or cycloalkadienyl ring; $R^1$ represents a hydrogen atom, a conventional penicillin blocking group or a conventional penicillin saltforming cation $R^2$ represents a substituted or unsubstituted alkylene, alkenylene, cycloalkylene, arylene, alkylenediaryl group; X and Y are individually an oxygen atom or a sulfur atom.

2. A compound represented by the general formula (Ia),

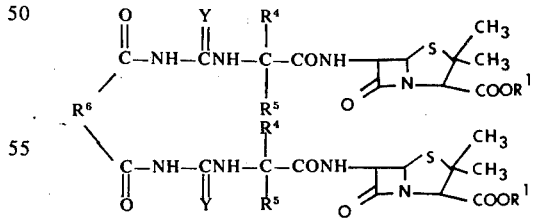

wherein $R^1$, Y and $R^4$ and $R^5$ are defined in claim 1 and $R^6$ represents a substituted or unsubstituted alkylene, alkenylene, cycloalkylene, arylene or alkylenediaryl group.

3. A compound according to claim 2, wherein $R^6$ is a substituted or unsubstituted alkylene, alkenylene or cycloalkylene group.

4. A compound according to claim 2, wherein $R^6$ is a substituted or unsubstituted arylene group.

5. A compound according to claim 2, wherein $R^6$ is an alkylenediaryl group.

6. A compound according to claim 1, wherein $R^1$ is a hydrogen atom.

7. A compound according to claim 1, wherein $R^1$ is selected from the group consisting of ester-forming groups capable of being removed by catalytic reduction, chemical reduction or hydrolysis under mild conditions and ester-forming groups capable of being easily removed owing to enzymes in a living body.

8. A compound selected from the group consisting of
N,N'-1-methyl-1-propylmalonyl-bis[6-(D(-)-α-ureidophenylacetamido) penicillanic acid],
N,N'-succinyl-bis[6-(D(-)-α-ureidophenylacetamido) penicillanic acid],
N,N'-glutaryl-bis[6-(D(-)-α-ureidophenylacetamido) penicillanic acid],
N,N'-adipoly-bis[6-(D(-)-α-ureidophenylacetamido) penicillanic acid],
N,N'-pimeloyl-bis[6-(D(-)-α-ureidophenylacetamido) penicillanic acid],
N,N'-sebacoyl-bis[6-(D(-)-α-ureidophenylacetamido) penicillanic acid],
N,N'-dodecanedioyl-bis[6-(D(-)-α-ureidophenylacetamido) penicillanic acid],
N,N'-tridecanedioyl-bis[6-(D(-)-α-ureidophenylacetamido) penicillanic acid],
N,N'-fumaroyl-bis[6-(D(-)-α-ureidophenylacetamido) penicillanic acid],
N,N'-1,4-cyclohexanedioyl-bis[6-(D(-)-α-ureidophenylacetamido) penicillanic acid],
N,N'-sebacoyl-bis[6-(D(-)-α-ureido-hydroxyphenylacetamido penicillanic acid],
N,N'-sebacoyl-bis[6-(1-ureidocyclohexylcarbonylamido) penicillanic acid],
N,N'-terephthaloyl-bis[6-(D(-)-α-ureidophenylacetamido) penicillanic acid],
N,N'-isophthaloyl-bis[6-(D(-)-α-ureidophenylacetamido) penicillanic acid],
N,N'-terephthaloyl-bis[6-(D(-)-α-thioureidophenylacetamido) penicillanic acid],
N,N'-2-nitroterephthaloyl-bis[6-(D(-)-α-ureidophenylacetamido) penicillanic acid],
N,N'-2,5-dimethoxyterephthaloyl-bis[6-(D(-)-α-ureidophenylacetamido) penicillanic acid], and
N,N'-2,6-naphthalenedioyl-bis[6-(D(-)-α-ureidophenylacetamido) penicillanic acid].

9. The compound N,N'-4,4'-ethylenedibenzoyl-bis[6-(D(-)-α-ureidophenylacetamido) penicillanic acid].

10. A compound selected from the group consisting of
dipivaloyloxymethyl N,N'-terephthaloyl-bis-[6-(D(-)-α-ureidophenylacetamido) penicillanate], and
diphthalidyl N,N'-sebacoyl-bis[6-(D(-)-α-ureidophenylacetamido) penicillanate].

11. A compound according to claim 1, wherein $R^1$ is a cation capable of forming a non-toxic salt.

12. A non-toxic salt of a compound according to claim 8.

13. N,N'-succinyl-bis[6-(D(-)-α-ureidophenylacetamido) penicillanic acid] or its non-toxic salt.

14. A pharmaceutical composition containing an active ingredient a compound of claim 1.

* * * * *